United States Patent [19]
Roberts et al.

[11] Patent Number: 5,344,424
[45] Date of Patent: Sep. 6, 1994

[54] SELECTIVELY RETRACTABLE, DISPOSABLE SURGICAL KNIFE

[76] Inventors: Philip L. Roberts, 7110 Pitt St., New Orleans, La. 70118; Mark L. Doerre, 4312 Fieldspoint Pl., Lexington, Ky. 40514

[21] Appl. No.: 30,758
[22] Filed: Mar. 12, 1993
[51] Int. Cl.⁵ ............................................. A61B 17/32
[52] U.S. Cl. ............................................. 606/167; 30/2; 30/162; 30/335
[58] Field of Search ............... 606/167, 170, 172, 181, 606/182, 185; 30/151, 162, 164, 167, 286, 335, 2; 128/751

[56] References Cited

U.S. PATENT DOCUMENTS

| | | |
|---|---|---|
| 1,888,488 | 11/1932 | Brown . |
| 1,906,573 | 5/1933 | Gits . |
| 1,960,130 | 5/1934 | Trubel . |
| 2,270,655 | 1/1942 | Keeran . |
| 2,854,745 | 10/1958 | Braverman . |
| 2,874,462 | 2/1959 | Benedict, Jr. et al. . |
| 3,187,431 | 6/1965 | Mattes . |
| 3,316,635 | 5/1967 | Merrow et al. . |
| 3,452,754 | 7/1969 | Stayer . |
| 3,453,729 | 7/1969 | Larson . |
| 3,765,089 | 10/1973 | Ibata . |
| 3,855,700 | 12/1974 | Gerson . |
| 3,879,847 | 4/1975 | Roll ................................. 30/335 |
| 3,906,626 | 9/1975 | Riuli . |
| 4,375,218 | 3/1983 | DiGeronimo . |
| 4,491,132 | 1/1985 | Aikins . |
| 4,516,575 | 5/1985 | Gerhard et al. . |
| 4,586,256 | 5/1986 | Weiman . |
| 4,621,425 | 11/1986 | Stoutenberg . |
| 4,730,613 | 3/1988 | Gordy . |
| 4,735,202 | 4/1988 | Williams . |
| 4,903,390 | 2/1990 | Vidal et al. . |
| 4,953,293 | 9/1990 | Sterlacci ............................ 30/151 |
| 5,139,507 | 8/1992 | Dolgin et al. ..................... 606/167 |
| 5,201,748 | 4/1993 | Newman et al. .................. 606/167 |
| 5,207,696 | 5/1993 | Matwijcow ........................ 30/151 |

FOREIGN PATENT DOCUMENTS 3722899  1/1989  Fed. Rep. of Germany ...... 606/167

*Primary Examiner*—Stephen C. Pellegrino
*Assistant Examiner*—William W. Lewis
*Attorney, Agent, or Firm*—King & Schickli

[57] ABSTRACT

A retractable, disposable surgical knife that includes a hollow sheath and a blade assembly received for sliding movement within the hollow sheath. The blade assembly includes a slide block and a knife blade held by the slide block. A mechanism including a cooperating resilient actuator and guide track allows the blade assembly to be selectively secured in a first, retracted position wherein the blade is withdrawn into the sheath and a second, extended position wherein the blade extends from the sheath for use. A separate mechanism is provided for permanently locking the blade assembly in a third, fully retracted position wherein blade is fully withdrawn within the sheath to prevent inadvertent sticks. The permanent locking mechanism is fully concealed within the sheath so as to prevent inadvertent engagement with an object and possible release from the permanently locked position.

15 Claims, 2 Drawing Sheets

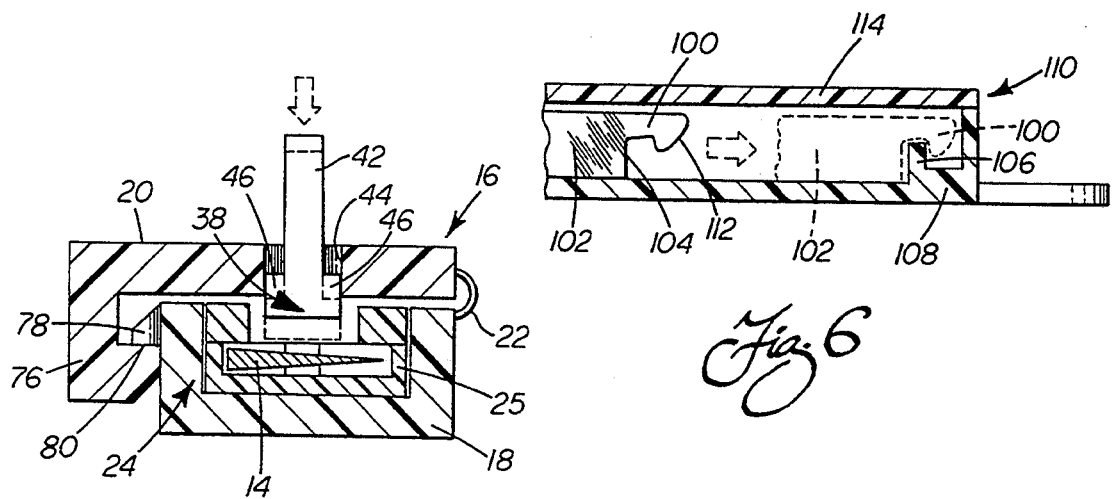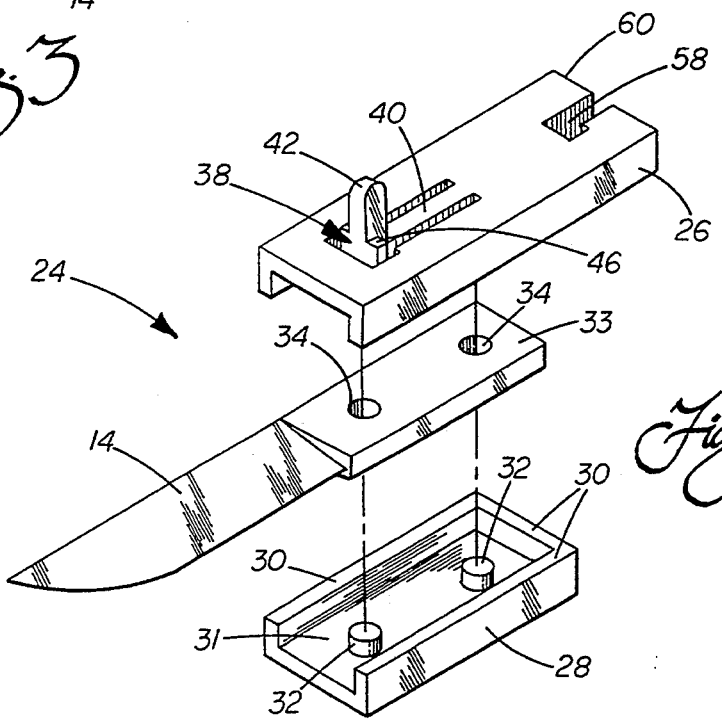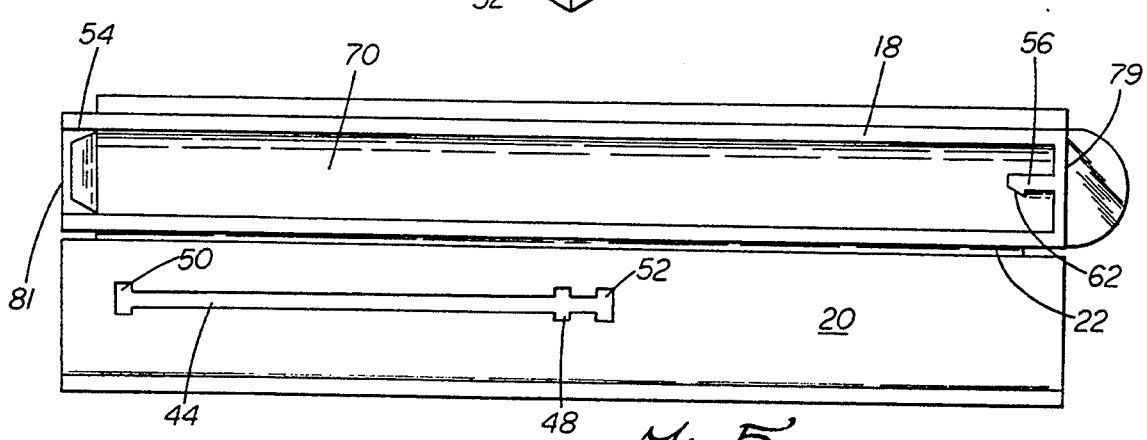

SELECTIVELY RETRACTABLE, DISPOSABLE SURGICAL KNIFE

TECHNICAL FIELD

The present invention relates generally to the medical instrument field and, more particularly, to a retractable and disposal surgical knife specifically designed to prevent inadvertent puncture wounds from the knife blade after use and, therefore, the spread of infectious disease.

BACKGROUND OF THE INVENTION

Surgical knives or scalpels are utilized by surgeons in many instances to complete operative procedures. Of course, many such procedures are performed on patients with infectious diseases such as acquired immune deficiency syndrome (AIDS) and infectious hepatitis. Unfortunately, the attending surgeons, nurses and other health care workers are subjected to a significant risk of infection if they are inadvertently stuck, pricked or cut with a contaminated surgical knife that has been withdrawn from a patient inflicted with such a communicable disease. Accordingly, it should be appreciated that it is critically important to avoid accidents including inadvertent sticks and cuts of any individual with a used surgical knife. Further, the safe, long term disposal of surgical knives and particularly used surgical knives is a serious concern.

These concerns have been addressed in the prior art. For example, in U.S. Pat. No. 3,906,626 to Riuli, a disposable surgical scalpel is disclosed including a protective outer sheath and retractable and extendable handle carrying a knife blade. The device also includes a "permanent" locking arrangement including a cooperating detent, spring, and resilient cam. It should be noted, however, that when locked the cam projects outwardly from the sheath. Accordingly, the cam may be engaged inadvertently by an object or individual and accidently manipulated to release the lock thereby allowing the knife blade to again be extended from the sheath. As a result, a significant risk of inadvertent or accidental sticks and cuts still remains in this prior art design. Accordingly, a need exists for an improved arrangement wherein the permanent lock is fully concealed and shielded from inadvertent contact and manipulation.

SUMMARY OF THE INVENTION

Accordingly, it is one object of the present invention to provide a retractable, disposal surgical knife of relatively simple construction that is inexpensive to produce.

Another object of the invention is to provide a retractable, disposal surgical knife that is relatively easy to utilize. More specifically, the knife may be readily switched from position to position and is of a shape and weight that allows comfortable gripping and precise manipulation when making an incision.

Still another object of the invention is to provide a retractable, disposable surgical knife that furnishes reliable, trouble free operation.

Yet another object of the invention is to provide a retractable, disposal surgical knife including a permanent locking mechanism that is fully concealed. Advantageously, the mechanism virtually prevents any possible inadvertent release of the device from the permanent lock position thereby virtually eliminating the risk of an individual receiving an inadvertent puncture wound.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved retractable, disposable surgical knife is provided. The surgical knife includes a hollow sheath and a blade assembly received for sliding movement within the hollow sheath. The blade assembly includes a slide block and a knife blade that is held in the slide block.

The surgical knife also includes means, mounted to the blade assembly and sheath, for selectively securing the blade assembly in a first, retracted position wherein the blade is withdrawn into the sheath and a second, extended position wherein the blade extends from the sheath for use. Additionally, the present surgical knife includes a separate means, also mounted to the blade and sheath, for permanently locking the blade assembly in a third, fully retracted position. In this position the blade is fully withdrawn within the protective sheath to prevent inadvertent sticks. Advantageously, the permanent locking mechanism is fully concealed within the sheath. This essentially prevents inadvertent engagement with an object or inadvertent manual manipulation and possible release from the permanently locked position. Accordingly, a more dependable and secure arrangement is provided than previously known in the art.

Still more specifically, the sheath includes a substantially three sided main body and an integral cover flap, for forming a fourth side, that is connected to the main body by a living hinge. Preferably the sheath is formed from a durable plastic by means of an injection molding process. As molded, the cover flap includes a locking flange provided with an inwardly projecting shoulder opposite the living hinge. Additionally, the main body includes a cooperating lip on the side of the main body opposite the living hinge and cover flap.

After positioning the blade assembly within the main body, the cover flap is folded over so as to overlap the main body with the projecting shoulder engaging under the lip. The shoulder and lip are then heat welded together to permanently seal the resulting four-sided sheath.

In accordance with still another aspect of the present invention, the selective securing means includes a resilient actuator carried on the blade assembly. This actuator extends through a cooperating guide slot formed in the cover flap so as to allow manipulation by the fingers of the operator. Of course, it should further be appreciated that the actuator and guide slot cooperate to limit the extent of movement of the blade assembly within the sheath.

More specifically, the resilient actuator includes a set of laterally protruding locking tabs and the guide slot includes at least two pair of matching notches for receiving the tabs when in the first retracted and second, extended positions. Additionally, it is preferred that a third pair of matching notches be provided for receiving the tabs when the blade assembly is positioned in a third, fully-retracted, permanent lock position. This is desirable as the positioning of the tabs in the third pair of matching notches provides the operator with a visual indication that the surgical knife is secured in the permanent lock position.

The permanent locking mechanism preferably includes a projecting hook that is integrally formed or molded with the main body of the sheath and a cooperating hook receiving cutout formed in the rear end of the slide block opposite the knife blade. More specifically, the cutout includes a latching shoulder that is engaged by the hook when in the third, permanently locked position. In an alternative embodiment, a hook is integrally formed projecting from the rear end of the slide block and a cutout with cooperating latching shoulder is integrally formed with the main body of the sheath. Of course, it should be appreciated that the cover flap fully conceals either embodiment of the permanent locking mechanism from view as well as potential inadvertent engagement with an object that could possibly lead to the release of the permanent lock. As a result, the security of the permanent lock is significantly enhanced over prior art designs and any risk of release of the permanent lock and possible inadvertent stick or cut of an individual is substantially eliminated.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing:

FIG. 3 is a cross-sectional view along line 3—3 in FIG. 2c through a mid-point of the surgical knife showing the main body and cover flap of the hollow sheath as well as the living hinge and connecting structure and the relative positioning of the slide block within the sheath;

FIG. 4 is an exploded view showing the blade assembly;

FIG. 5 is a plan view showing the hollow sheath, with cover flap open, ready to receive the blade assembly; and FIG. 6 is a fragmentary, partially sectional, side elevational view of an embodiment of the permanent locking mechanism incorporated in the surgical knife of the present invention.

Figure 1:
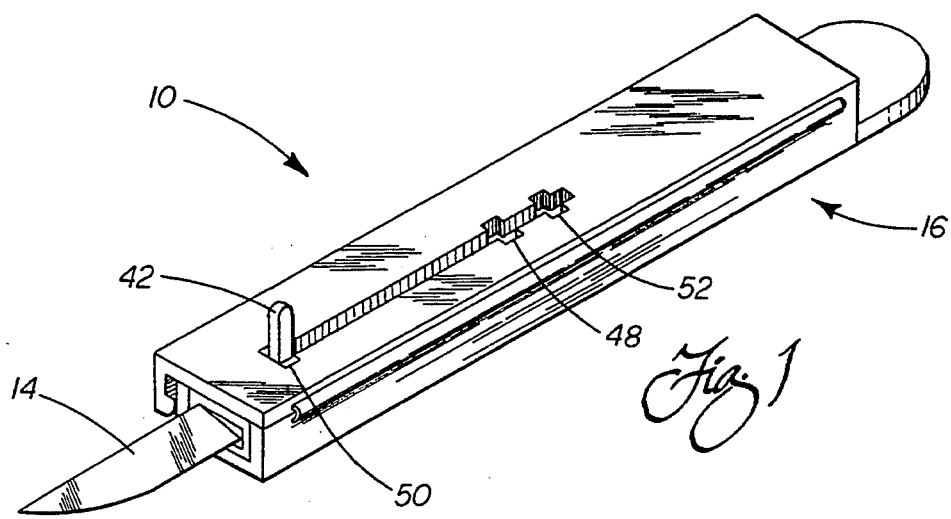
FIG. 1 is a perspective view of the retractable, disposable surgical knife of the present invention in the second, extended position for surgical incising.

Reference will now be made in detail to the present preferred embodiment of the invention, an example of which is illustrated in the accompanying drawing.

DETAILED DESCRIPTION OF THE INVENTION

Reference is now made to the drawing FIGS. 1-5 showing the improved surgical knife 10 of the present invention. As will be more fully understood after reviewing the entire description, the surgical knife 10 advantageously includes a fully shielded or concealed permanent locking mechanism 12 that virtually prevents inadvertent engagement and release so as to ensure that the blade 14 is maintained in a retracted position thereby preventing inadvertent sticks and cuts.

As shown best in FIGS. 3 and 5, the surgical knife 10 includes a sheath 16 having a substantially three-sided main body 18 and a cover flap 20 of substantially L-shaped cross-section. Preferably, both the main body 18 and cover flap 20 of the sheath 16 are molded from durable plastic utilizing an injection molding process. Advantageously, both the materials and the process itself are relatively inexpensive so as to allow economic production. Additionally, this process allows the formation of a living hinge 22 between the main body 18 and cover flap 20 whereby these two components are formed as a single, integral part.

A blade assembly 24 is received for sliding movement within the sheath 16 (note FIGS. 3 and 4). More specifically, the blade assembly 24 includes a slide block 25 that holds the blade 14. As best shown in FIG. 4, the slide block 25 includes a cooperating upper section 26 and lower section 28 that may be also molded from plastic. As particularly shown, the lower section 28 includes a series of three flanges 30 that form a substantially U-shaped cavity 31 corresponding in profile to the rear or mounting portion 33 of the knife blade 14 but allowing clearance for receipt therein. Additionally, two upstanding pins 32 are provided. These pins 32 are received in cooperating apertures 34 in the knife blade mounting portion 33. Together, the flanges 30 and pins 32 cooperate with the lower face of the upper section 26 to secure the knife blade 14 in position in the slide block 25 when the upper section 26 and the lower section 28 are heat welded together. As play between the knife blade 14 and slide block 25 is essentially eliminated, a precise incision may be made when utilizing the surgical knife 10.

Figure 2A:
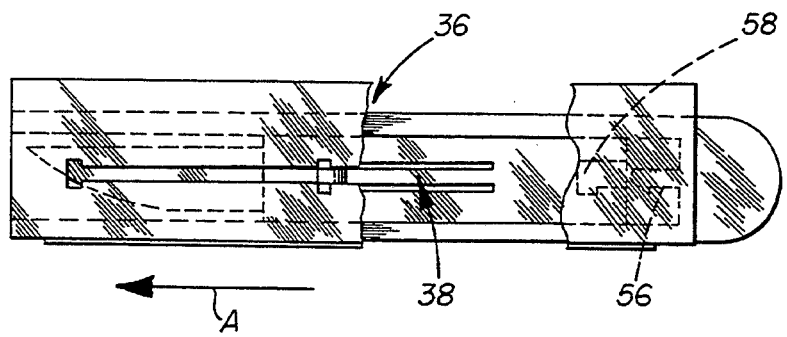
FIGS. 2a-2c are top plan views showing, respectively, the surgical knife of FIG. 1 partially cut away in a first, retracted position; in a second, fully extended position for use; and partially cut away in a third, fully retracted position wherein the permanent lock is engaged.

In accordance with an important aspect of the present invention, the blade assembly 24 and, accordingly, the knife blade 14 may be fully retracted into and/or extended from the sheath 16 as desired. Further, the blade assembly 24 may be secured in the necessary position relative to the sheath 16 so as to allow easy, convenient and reliable operation. The securing mechanism for achieving this end is generally shown in FIGS. 2a-2c and is designated reference numeral 36.

More specifically, a resilient actuator 38 is integrally formed when molding the upper section 26 of the slide block 25. The actuator 38 includes a relatively narrow leg portion 40 that supports on its distal end an upstanding knob 42 for finger actuation. When assembled, the upstanding knob 42 extends through a guide slot 44 formed in the cover flap 20 of sheath 16. As should be appreciated, the ends of the guide slot engage the upstanding knob 42 and function to limit the extent of the sliding action of the blade assembly 24 within the sheath 16.

Additionally, it should be appreciated that laterally spaced locking tabs 46 are provided adjacent the upstanding knob 42 on the resilient actuator 38. These locking tabs 46 engage in a series of notches 48, 50, 52 positioned at spaced intervals along the guide slot 44. More specifically, when the locking tabs 46 are positioned to engage in the first notch 48, the blade assembly 24 is secured in a first, retracted position wherein the blade 14 is fully contained within the sheath 16 (see FIG. 2a). This is the position in which the surgical knife 10 is packaged for shipment to the user.

Figure 2B:
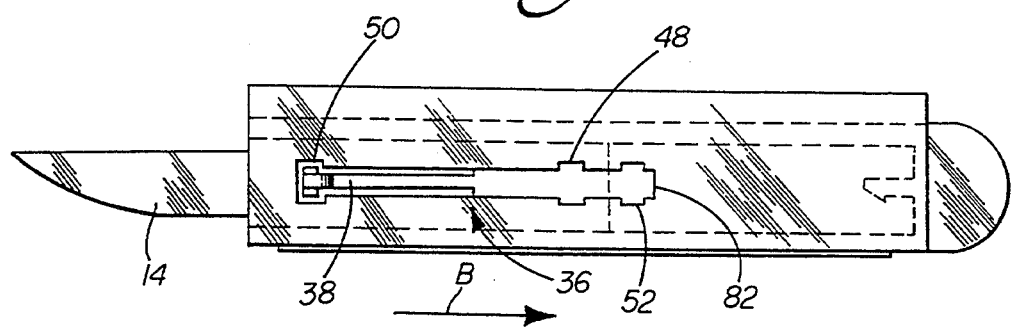
Figure 2C:
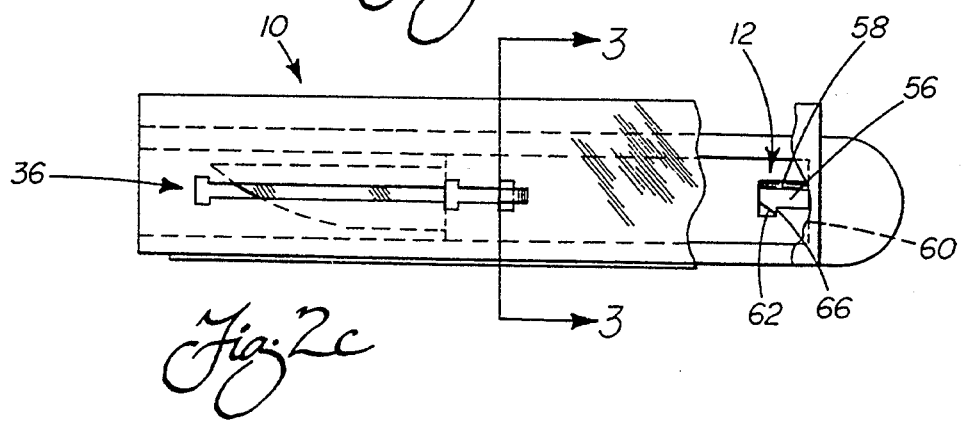

In contrast, when the locking tabs 46 are positioned to engage in the second notch 50, the blade assembly 24 is positioned so that the blade 14 fully extends from the sheath 16 (see FIG. 2b). In this position, the user may surgically incise a patient as required. Of course, as the blade 14 is secured substantially free of play in the slide block 25 and the slide block 25 is securely held substantially free of play within the sheath 16 (note converging cam surfaces 54 shown best in FIG. 5 that serve to pinch and tightly hold the slide block 25 when in the second, operative position), precision incising is possible.

Following completion of the operative procedure, the upstanding knob 42 is manipulated to fully retract the blade assembly 24 to a third, retracted position (see FIG. 2c). In this fully retracted position, the blade assembly 24 is permanently locked in position in the manner described below with the blade 14 fully received within the protective sheath 16. This allows safe disposal of the surgical knife 10 while minimizing the risk of the inadvertent release of the locking mechanism 12 and, therefore, the potential for inadvertent sticks and cuts that could lead to the communication of infectious disease.

The permanent locking mechanism 12 is best shown with reference to FIGS. 2a and 2c. Particularly, a hook 56 is integrally formed on and molded with the main body 18 of the sheath 16 (see also FIG. 5). Similarly, a cooperating cutout 58 is integrally formed in the upper section 26 of the slide block 25 (see also FIG. 4). More particularly, the cutout 58 communicates with the rear face 60 of the slide block 25 opposite the projecting knife blade 14.

When the blade assembly 24 is in the first, retracted position, the hook 56 is not engaged in the cutout 58 and, accordingly, the permanent lock is not engaged (note FIG. 2a). Accordingly, an individual is able to manipulate the blade assembly 24 to the second, operative position as required to complete the surgical procedure. In contrast, when the upstanding knob 42 is manipulated to the rearmost position so as to bring the locking tabs 46 into engagement with the third notch 52, the cam surface 62 engages the rear face 60 of the slide block 25 and the hook 56 pivots away and passes into the cutout 58. As soon as the hook 56 reaches the wide portion of the cutout 58 the resilient nature of the material causes the hook to pivot into engagement with the shoulder 66 thereby securing the slide block 25 into position. As the hook 56 and cutout 58 are fully concealed and shielded by the overlying cover flap 20, no objects or fingers may inadvertently engage the locking mechanism 12 and, accordingly, a virtual permanent lock results. Thus, inadvertent release of the permanent lock is substantially avoided.

First the assembly procedure and then the utilization of the surgical knife 10 of the present invention will now be described.

After molding the upper and lower sections 26, 28 of the slide block 25, the blade 14 is carefully positioned in the cavity 31 of the lower section defined by the three cooperating flanges 30. As this is done, the pins 32 project through the corresponding apertures 34 in the blade 14. Next, the upper section 26 of the slide block 25 is placed in position over the lower section 28 where it is heat welded to secure in position.

The completed blade assembly 24 is then positioned within the three walls of the main body 18 by placing in the open face 72 (see FIG. 5). The cover flap 20 is then folded over about the living hinge 22 so as to close the main body 18 and form the fourth wall of the sheath 16. As this is done, the upstanding knob 42 is threaded into the guide slot 44 and the locking flange 76 on the cover flap 20 is snapped over the lip 78 on the main body 18. The shoulder 80 on the locking flange 76 engages the lower side of the lip 78 to secure the cover flap 20 in the closed position. When closed, closed end 79 of the sheath 16 and the cover flap 20 fully conceal and shield the locking mechanism 12 from view and inadvertent manipulation and release. As a further precaution to ensure that the cover flap 20 remains closed, the locking flange 76 and lip 78 may be heat welded together for permanency.

If not already so positioned, the upstanding knob 42 is now manipulated to position the blade assembly 24 in the first retracted position with the locking tabs 46 received in the first notch 48. In this way, the blade 14 is fully retracted within the sheath 16 so that inadvertent sticks and cuts are avoided but selective movement to the second, extended position is still possible. The surgical knife 10 is then sterilized and packaged in a manner known in the art.

As indicated above, the surgical knife 10 of the present invention is particularly easy to utilize. The surgical knife is first removed from packaging and the blade assembly 24 is maintained in the first, retracted position until ready to complete the surgical procedure. At that point in time, the surgeon presses downwardly on the upstanding knob 42; the resilient leg portion 40 allowing sufficient limited downward movement to allow the locking tabs 46 to pass under the cover flap 20.

Once the clearance is provided, the upstanding knob 42 is pushed in the direction of action arrow A (see FIG. 2a) while maintaining downward pressure. As a result, the blade assembly 24 slides forward in the sheath 16 and the blade 14 is extended from the open end 81. Upon the upstanding knob 42 reaching the forward end of the guide slot 44, the knob is released. As a result, the resilient leg portion 40 springs back to its natural position thereby bringing the locking tabs 46 into engagement in the second notch 50. This serves to secure the blade assembly 24 in the second, extended position shown in FIG. 2b. In this position, the slide block 25 is securely held by the squeezing engagement of the converging cam surfaces 54 and extended from the sheath 16 to allow precise incising in the manner desired.

Following utilization, the upstanding knob 42 is again depressed to allow passage of the cams 46 under the cover flap 20 and simultaneously moved in the direction of action arrow B (see FIG. 2b). Typically, the rearward movement will continue until the blade assembly 24 is fully retracted to the third, retracted position wherein the locking tabs 46 are received in the third notch 52 and the permanent locking mechanism 12 is engaged (that is, the hook 56 is engaged in the cutout 58 as shown in FIG. 2c). Advantageously, the receipt of the locking tabs 46 in the third notch 52 provides visual confirmation of the engagement of the permanent lock indicating to the user that the surgical knife 10 is ready for safe disposal. A slot extension 82 positively insures that full engagement. Of course, it should be recognized that in certain situations, retraction to only the first, retracted position is all that is desired so that the blade assembly 24 may again be extended for additional, subsequent incising.

An alternative embodiment for the permanent locking mechanism 12 is shown in FIG. 6. More specifically, a hook 100 is integrally molded with the slide block 102 so as to project rearwardly from the rear wall 104 of the slide block. The hook 100 opens downwardly and cooperates with the latching shoulder 106 integrally molded in the main body 108 of the sheath 110. Accordingly, as the slide block 102 is moved into the rearmost, permanent locking position, the leading cam surface 112 engages the latching shoulder 106. This pivots the hook 100 upwardly over the latching shoulder 106 until the hook clears the shoulder. The resilient hook 100 then snaps downwardly with the hook in full, virtually permanent and nondefeatable engagement with the shoulder 106 (note phantom line position). Of course, the main body 108 and cover flap 114 of the sheath 110 fully conceal and protect the locking mechanism 12 as already described with respect to the original embodiment.

In summary, numerous benefits have been described which result from employing the concepts of the present invention. Advantageously, the surgical knife 10 incorporates a relatively simple structure that may be quickly, efficiently and economically produced and assembled. Additionally, the surgical knife 10 allows very simple, straight-forward operation. Further, the permanent locking mechanism 12 provided for the purposes of disposal is fully concealed by the cover flap 20 that is heat welded in position. Accordingly, manipulation of the permanent locking mechanism 12 and release thereof is substantially prevented.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with breadth to which they are fairly, legally and equitably entitled.

We claim:

1. A retractable, disposable surgical knife, comprising:
   a hollow sheath;
   a blade assembly received for sliding movement within said sheath, said blade assembly including a slide block and a knife blade held by said slide block;
   means, mounted to said blade assembly and sheath, for selectively securing said blade assembly in a first, retracted position wherein said blade is withdrawn into said sheath and a second, extended position wherein said blade extends from said sheath for use; and
   means, mounted to said blade assembly and sheath, for permanently locking said blade assembly in a third, fully retracted position wherein said blade is fully withdrawn within said sheath to prevent inadvertent sticks, said permanent locking means being fully concealed and contained within said sheath so as to prevent inadvertent engagement with an object and possible release from the permanently locked position.

2. The surgical knife set forth in claim 1, wherein said sheath includes a three-sided main body and a cover flap connected to said main body by a living hinge.

3. The surgical knife set forth in claim 2, wherein said cover flap includes a locking flange with inwardly projecting shoulder opposite said living hinge and said main body includes a cooperating lip on a side opposite said living hinge and cover flap.

4. The surgical knife set forth in claim 3, wherein said main body and cover flap are formed from plastic and said cover flap is folded over said main body with said projecting shoulder engaging under said lip and said projecting shoulder and lip are heat welded together to permanently seal said sheath.

5. The surgical knife set forth in claim 2, wherein said selective securing means includes a resilient actuator carried on said blade assembly and a cooperating guide slot formed in said cover flap.

6. The surgical knife set forth in claim 5, wherein said resilient actuator includes a set of laterally protruding locking tabs and said guide slot includes at least two cooperating notches for receiving said tabs when said blade assembly is, respectively, in the first, retracted position and the second, extended position.

7. The surgical knife set forth in claim 2, wherein said permanent locking means includes a projecting hook integrally formed on said main body and a cooperating hook receiving cutout formed in a rear end of said slide block opposite said knife blade, said cutout including a shoulder engaged by said hook when in said third, permanently locked position.

8. The surgical knife set forth in claim 7, wherein said hollow sheath has a single closed end and said closed end and cover flap conceal said hook and cutout from view and inadvertent engagement with an object.

9. The surgical knife set forth in claim 6, wherein said permanent locking means includes a projecting hook on said main body and a cooperating hook receiving cutout formed in a rear end of said slide block opposite said knife blade, said cutout including a shoulder engaged by said hook when in said third, permanently locked position.

10. The surgical knife set forth in claim 9, wherein said hollow sheath has a single closed end and said closed end and cover flap conceal said hook and cutout from view and inadvertent engagement with an object.

11. The surgical knife set forth in claim 10, wherein said hollow sheath includes an open end and converging surfaces adjacent said open end for squeezing and gripping said blade assembly.

12. The surgical knife set forth in claim 1, wherein said hollow sheath includes an open end and converging surfaces adjacent said open end for squeezing and gripping said blade assembly.

13. The surgical knife set forth in claim 6, wherein said permanent locking means includes a projecting hook on said slide block and a cooperating latching shoulder on said main body whereby engagement of said hook with said latching shoulder occurs in said third, permanently locked position.

14. The surgical knife set forth in claim 13, wherein said hollow sheath has a single closed end and said closed end and cover flap conceal said hook and latching shoulder from view and inadvertent engagement with an object.

15. The surgical knife set forth in claim 13, wherein said hollow sheath includes an open end and converging surfaces adjacent said open end for squeezing and gripping said blade assembly.

* * * * *